US008481479B1

(12) United States Patent
Mousa (10) Patent No.: US 8,481,479 B1
(45) Date of Patent: Jul. 9, 2013

(54) FORMULATIONS OF FACTOR VIIA INHIBITORS AND UTILITY

(76) Inventor: Shaker A. Mousa, Wynantskill, NY (US)

( * ) Notice: Subject to any disclaimer, the term of this patent is extended or adjusted under 35 U.S.C. 154(b) by 0 days.

(21) Appl. No.: 13/414,106

(22) Filed: Mar. 7, 2012

(51) Int. Cl.
*A61K 38/00* (2006.01)
*A61K 38/05* (2006.01)
*C07K 14/755* (2006.01)

(52) U.S. Cl.
USPC ........... 514/1.1; 514/13.5; 514/13.7; 514/802

(58) Field of Classification Search
None
See application file for complete search history.

(56) References Cited

U.S. PATENT DOCUMENTS

2007/0122440 A1* 5/2007 Macosko et al. .............. 424/405
2008/0286372 A1* 11/2008 Pacetti et al. ................. 424/493

OTHER PUBLICATIONS

Krishnan, R., et al. "Probing the S2 site of factor VIIa to generate potent and selective inhibiors: the structure of BCX-3607 in complex with tissue factor-factor VIIa," Acta Cryst. D63:689-697 (2007).*
Miura, M., et al. "Potent and selective TF/FVIIa inhibitors containing a neutral P1 ligand." Bioorg. Med. Chem 14:7688-7708 (2006).*
Hu, H., et al., "Potent 4-amino-5-azaindole factor VIIa inhibitors," Bioorg. Med. Chem 16:4567-4570 (2006).*
Krishnan, et al., "Probing the S2 site of factor VIIa to generate potent and selective inhibitors: the structure of BCX-3607 in complex with tissue factor-factor VIIa" Acta Crystallographica D63: 689-697 (2007)—copy provided in OA mailed Oct. 3, 2012.*

* cited by examiner

*Primary Examiner* — Christina Bradley
*Assistant Examiner* — Kristina M Hellman
(74) *Attorney, Agent, or Firm* — Schmeiser, Olsen & Watts, LLP

(57) ABSTRACT

A nanoparticle, a chemical structure, and a treatment method for treating a patient having a disorder. The nanoparticle includes a poly L-arginine polymer and a Factor VIIa inhibitor conjugated to or encapsulated in the poly L-arginine polymer. The chemical structure includes a Factor VIIa inhibitor that includes at least one nitric oxide (NO) donor. The treatment method administers a therapeutic effective amount of the nanoparticle or chemical structure to the patient to treat the disorder. The disorder may be a vascular disorder, pulmonary hypertension, cardiac insufficiency, a neurological disorder, and combinations thereof.

7 Claims, 5 Drawing Sheets

FORMULATIONS OF FACTOR VIIA INHIBITORS AND UTILITY

FIELD OF THE INVENTION

The field relates to novel nanoparticle formulations that include vasodilator Factor VIIa inhibitors, and to their use in treatment of disorders in a patient, the disorders including pulmonary hypertension, pulmonary arterial hypertension, vascular endothelial dysfunction-mediated disorders, and other vascular diseases and disorders.

BACKGROUND OF THE INVENTION

Vascular endothelial-mediated disorders including sickle cell diseases, tissue ischemia, and circulatory disorders represent a major medical dilemma and treatment of these disorders represents an unmet clinical need. Additionally, other major vascular disorders with unmet clinical needs include pulmonary hypertension (PH) and a form of PH called pulmonary arterial hypertension (PAH). PH is a disorder characterized by abnormally high blood pressure in the lungs. Further, the narrowing of vasculature that occurs in many of these diseases causes the buildup of pressure and the heart must work harder in order to force blood through the pulmonary arteries. PH is an increase in blood pressure in the pulmonary artery, pulmonary vein, and/or pulmonary capillaries. PH is a very serious condition, potentially leading to shortness of breath, dizziness, fainting, decreased exercise tolerance, heart failure, pulmonary edema, and death. PH is generally characterized by a mean pulmonary artery pressure exceeding 25 mm Hg (3300 Pa) at rest or 30 mm Hg (4000 Pa) with exercise and the World Health Organization (WHO) has subdivided PH into five different groups:

WHO Group I—Pulmonary arterial hypertension (PAH)
  Idiopathic (IPAH)
  Familial (FPAH)
  Associated with other diseases (APAH): collagen vascular disease (e.g. scleroderma), congenital shunts between the systemic and pulmonary circulation, portal hypertension, HIV infection, drugs, toxins, or other diseases or disorders
  Associated with venous or capillary disease
WHO Group II—Pulmonary hypertension associated with left heart disease
  Atrial or ventricular disease
  Valvular disease (e.g. mitral stenosis)
WHO Group III—Pulmonary hypertension associated with lung diseases and/or hypoxemia
  Chronic obstructive pulmonary disease (COPD), interstitial lung disease (ILD)
  Sleep-disordered breathing, alveolar hypoventilation
  Chronic exposure to high altitude
  Developmental lung abnormalities
WHO Group IV—Pulmonary hypertension due to chronic thrombotic and/or embolic disease
  Pulmonary embolism in the proximal or distal pulmonary arteries
  Embolization of other matter, such as tumor cells or parasites
WHO Group V—Miscellaneous PH involves the vasoconstriction or tightening of blood vessels connected to and within the lungs. This tightening makes it harder for the heart to pump blood through the lungs, much as it is harder to make water flow through a narrower pipe as opposed to a wider pipe. Over time, the blood vessels affected by this vasoconstriction become both stiffer and thicker, in a process known as fibrosis. This fibrosis further increases the blood pressure within the lungs and impairs blood flow. In addition, the increased workload of the heart causes thickening and enlargement of the right ventricle, making the heart less able to pump blood through the lungs, causing right heart failure. As blood flowing through the lungs decreases, the left side of the heart receives less blood and this blood may also carry less oxygen than normal. Therefore it becomes harder and harder for the left side of the heart to pump to supply sufficient oxygen to the rest of the body, especially during physical activity.

In pulmonary venous hypertension (WHO Group II) there is not necessarily any obstruction to blood flow in the lungs. Instead, the left heart fails to pump blood efficiently out of the heart into the body, leading to pooling of blood in veins leading from the lungs to the left heart (congestive heart failure). This causes pulmonary edema and pleural effusions. The fluid build-up and damage to the lungs may also lead to hypoxia and consequent vasoconstriction of the pulmonary arteries, so that the pathology may come to resemble that of Group I or III.

In hypoxic pulmonary hypertension (WHO Group III), the low levels of oxygen may cause vasoconstriction or tightening of pulmonary arteries. This leads to a similar pathophysiology as PAH.

In chronic thromboembolic pulmonary hypertension (WHO Group IV), the blood vessels are blocked or narrowed with blood clots. Again, this leads to a similar pathophysiology as pulmonary arterial hypertension.

The pathogenesis of PH involves a complex and multifactorial process. Endothelial dysfunction seems to play an integral role in mediating the structural changes in the pulmonary vasculature that occur as a result of PH. These dysfunctions include disordered endothelial cell proliferation and concurrent neoangiogenesis. When this angiogenesis is exuberant, it results in the formation of glomeruloid structures known as plexiform lesions. In addition, a decrease in the vasodilators nitric oxide (NO) and prostacyclin, along with an increase in vasoconstrictors such as endothelin-1 (ET-1), serotonin, and thromboxane, have been observed in patients with PH. Because most of these mediators affect the growth of the smooth muscle cells, an alteration in their production or expression may facilitate the development of pulmonary vascular hypertrophy and the structural remodeling of the vasculature that is characteristic of PH. It is conceivable that the beneficial effects of many of the treatments currently available for PH, such as the use of prostacyclin, NO, and ET-1 antagonists, result at least in part from restoring the balance between these mediators.

In addition to the potential consequences of an imbalance in the endothelial production of various mediators, injury to the endothelium caused by PH may expose the underlying vascular tissue to diverse blood-borne factors that may further promote pathological changes. Endothelial dysfunction may also have adverse consequences on pulmonary vascular hemostasis by altering the production of anticoagulant factors. Recent reports of genetic mutations in the endothelial cells of patients with PH further underscore the role of these cells in the disease pathogenesis.

Available evidence suggests that NO is at least partially responsible for resting pulmonary vasorelaxation. Endothelial NO synthetase (eNOS) catalyzes the conversion of L-arginine to citrulline, producing NO. In addition, NO activates guanylate cyclase and increases cyclic guanine mono phosphate (cGMP) levels in smooth muscle cells, causing vasodilatation. The specific role of eNOS in pulmonary vascular tone regulation is best demonstrated in animal models. Overproduction of eNOS in transgenic mice prevents hypoxia-induced PH (3, 4).

Tissue factor (TF) is a transmembrane glycoprotein that initiates the coagulation cascade when complexed with factor VIIa and may also participate in angiogenesis. In situ thrombosis occurs in severe PH, and there are several reports linking platelet activation to the etiology of severe disease. TF has also been shown to regulate intimal hyperplasia in response to systemic arterial injury. The TF and factor VIIa complex (TF/VIIa) might play a key role in the disordered angiogenesis and intimal hyperplasia seen in PH. Lung sections from PH lung immunostained with an antibody to TF showed that alveolar epithelium and bronchi stained abundantly for TF. TF was not seen in normal pulmonary arterial vascular cells. In contrast, animals with PH had modest TF staining in diseased vessels and more pronounced TF staining in the plexiform-like lesions. The disordered angiogenesis and neointimal lesions of severe human disease might be mediated via the TF/VIIa pathway and this approach may be a better model for the vascular pathology of moderate to severe human PH. Over-expression of Tissue Factor Pathway Inhibitor (TFPI) in pulmonary vascular beds results in improved hemodynamic performance and reduced pulmonary vascular remodeling in a murine model of hypoxia-induced PH. This improvement is in part due to autocrine and paracrine effects of TFPI overexpression.

For WHO Group II pulmonary hypertension, the first approach is to optimize left ventricular function by the use of diuretics, beta blockers, Angiotension Converting Enzyme (ACE) inhibitors, etc., or to repair/replace the mitral valve or aortic valve. Where there is PAH, treatment is more challenging, and may include lifestyle changes. Treatment of PAH with digoxin, diuretics, oral anticoagulants, and oxygen therapy are conventional, but not highly effective. Newer drugs targeting the pulmonary arteries include endothelin receptor antagonists (e.g., bosentan, sitaxentan, ambrisentan), phosphodiesterase type 5 inhibitors (e.g., sildenafil, tadalafil), prostacyclin derivatives (e.g., epoprostenol, treprostenil, iloprost, beroprost), and soluble guanylate cyclase (sGC) activators (e.g., cinaciguat and riociguat). One surgical approach to PAH treatment is atrial septostomy to create a communication between the right and left atria, thereby relieving pressure on the right side of the heart, but at the cost of lower oxygen levels in blood (hypoxia). Other surgical approaches include lung transplantation and pulmonary thromboendarterectomy (PTE) to remove large clots along with the lining of the pulmonary artery.

There is thus an unmet need for improved treatments for PH, particularly PAH, for cardiac insufficiency due to partial or complete blockage of coronary arteries and/or damage due to myocardial infarction (e.g., acute or congestive heart failure and acute myocardial infarction). There is moreover a need for a means of delivering factor VIIa inhibitors on a sustained basis to treat such conditions.

SUMMARY OF THE INVENTION

The present invention provides a nanoparticle, comprising a poly L-arginine polymer and a Factor VIIa inhibitor conjugated to or encapsulated in the poly L-arginine polymer.

The present invention provides a chemical structure, comprising a Factor VIIa inhibitor that includes at least one nitric oxide (NO) donor.

The present invention provides a method of treating a patient having a disorder, said method comprising administering a therapeutic effective amount of the nanoparticle or chemical structure of the present invention to the patient to treat the disorder, wherein the disorder is selected from the group consisting of a vascular disorder, cardiac insufficiency, a neurological disorder, and combinations thereof.

DETAILED DESCRIPTION OF THE INVENTION

The examples and drawings provided in the detailed description are merely examples, which should not be used to limit the scope of the claims in any claim construction or interpretation.

Pulmonary hypertension (PH) and pulmonary arterial hypertension (PAH) are commonly recognized complication of chronic respiratory disease. Enhanced vasoconstriction, pulmonary vascular remodeling and in situ thrombosis contribute to the increased pulmonary vascular resistance observed in PH associated with hypoxic lung disease. The tissue factor/factor VIIa pathway regulates fibrin deposition in response to acute and chronic vascular injury, which can be modulated by factor VIIa inhibitors. Having NO donor within the structure of Factor VIIa inhibitor or formulating Factor VIIa inhibitor in a polyarginine nanoparticle (i.e., a nanoparticle comprising a poly L-arginine polymer) according to the present invention provides dual function in attacking this complex disorder as well as other vascular disorders including sickle cell, peripheral artery diseases, critical limb ischemia, acute coronary syndrome, stroke, and other vasoconstrictor or pro-thrombotic-mediated disorders.

Factor VIIa inhibitors—NO (i.e., a chemical structure, comprising a Factor VIIa inhibitor that includes at least one nitric oxide (NO) donor) donor and its nanoformulations dilate the cardiac arteries and enhance cardiac function. Factor VIIa inhibitors—NO donor are therefore useful for treating acute myocardial infarction and for treating heart failure resulting from myocardial infarction. In one embodiment, the Factor VIIa inhibitors or Factor VIIa inhibitors—NO donor are encapsulated or covalently bonded to poly L-arginine (PLA) or the above-modified poly L-arginine nanoparticles can be used in a drug-eluting stent (e.g., for patients having had or at risk of acute myocardial infarction) such as for insertion in the coronary artery.

The present invention provides inhalable (for example, aerosol therapy using micro spray techniques), oral, or injectable Factor VIIa inhibitors containing NO donor nanoparticle formulations, wherein the Factor VIIa inhibitor containing NO donor is encapsulated into bio-degradable polymers that release L-arginine that is converted to Nitric Oxide for vasodilatation.

In one embodiment, a nanoparticle of the present invention comprises a poly L-arginine polymer and a Factor VIIa inhibitor, wherein the Factor VIIa inhibitor either includes or does not include a nitric oxide (NO) donor.

In one embodiment, the polymer comprises poly-L-arginine.

In one embodiment, the polymer comprises poly-L-arginine bonded to fatty acids.

In one embodiment, the polymer comprises poly-L-arginine cross-linked with gluteraldehyde.

In one embodiment, the polymer comprises poly-L-arginine linked to bile acids.

In one embodiment, the polymer comprises poly-L-arginine linked to hyaluronic acid.

In one embodiment, the polymer comprises poly-L-arginine linked to low molecular to ultra low molecular weight chitosan.

In one embodiment, the polymer comprises poly-L-arginine linked to other amino acids such as tyrosine, L-Lysine, etc.

In one embodiment, the polymer comprises poly-L-arginine linked to PLGA. Where in PLGA could be poly (D,L-lactide-co-glycolide) (PLGA) and poly(vinyl sulfonate-co-vinyl alcohol).

In one embodiment, the polymer comprising poly-L-arginine linked to the above moieties is conjugated to a site directed probe that recognizes pulmonary tissues and compromised vascular tissues for homing the active compound into lung tissue and deep penetration into pulmonary tissues.

In one embodiment, the nanoparticles have an average diameter in a range of 50-1000 nm; e.g., 100-500 nm or 50-250 nm.

In one embodiment, the nanoparticles have a zeta potential of 0 to 100 mV (e.g., 0 to +50 mV).

In one embodiment, the Factor VIIa inhibitors are conjugated to (e.g., by being covalently linked to) the poly L-arginine polymer.

In one embodiment, the Factor VIIa inhibitors are encapsulated in the poly-L-arginine polymer and not covalently linked to the poly L-arginine polymer.

In one embodiment, the formed nanoparticles are coated with polyethylene glycol (PEG), bile salt, lipid, or other permeation enhancers/stabilizers.

In one embodiment, the formed poly-L-arginine nanoparticles are encapsulated in liposomes with sizes in the 1-100 micrometer ranges (e.g., 10-20 micrometers).

In one embodiment, the present invention provides a nanoparticle that comprises a poly L-arginine polymer and a Factor VIIa inhibitor conjugated to or encapsulated in in the L-arginine polymer, wherein the Factor VIIa inhibitor includes a nitric oxide (NO) donor. In one example, the Factor VIIa inhibitor is conjugated to the poly L-arginine polymer by being covalently bonded to the poly L-arginine polymer. In one example, the Factor VIIa inhibitor is encapsulated in the poly L-arginine polymer and not covalently bonded to the poly L-arginine polymer. In one example, the poly L-arginine polymer is cross-linked with at least one substance selected from the group consisting of chitosan, lactic-co-gylycolic acid (PLGA), fattiy acids, bile acids, amino acids, and combinations thereof.

In one embodiment, the present invention provides a nanoparticle that comprises a poly L-arginine polymer and a Factor VIIa inhibitor, wherein the Factor VIIa inhibitor does not include a nitric oxide (NO) donor.

In one embodiment, the present invention provides a chemical structure, wherein the chemical structure comprises a Factor VIIa inhibitor that includes at least one nitric oxide (NO) donor.

In one embodiment, the present invention provides a treatment method of treating a patient having a disorder, wherein the treatment method comprises administering a therapeutic effective amount of a nanoparticle or chemical structure of the present invention to the patient to treat the disorder, and wherein the disorder is a vascular disorder, cardiac insufficiency, a neurological disorder, or combinations thereof. In one example, the vascular disorder comprises pulmonary hypertension (e.g., pulmonary arterial hypertension).

In one embodiment, the Factor VIIa inhibitor nanoparticle formulation may be made from one or more Factor VIIa inhibitors and at least one component of the following components:

Poly L-Arginine;

Chitosan

PLGA;

PVA (stabilizer);

Polyethylene glycol;

Liposome.

In one example, the components in the nanoparticle formulation are as described in Table 1 infra.

TABLE 1

Components of the Nanoparticle Formulation

| Components of the Nanoparticle Formulation | Approximate Amount (weight percent) in the Nanoparticle Formulation | Role in the Nanoparticle Formulation |
|---|---|---|
| L-arginine | 50-70%, e.g. 60% | Component of the nanoparticle |
| Fatty acids, bile acids, amino acids, PLGA, Chitosan (each cross-linked with L-arginine) | 10-20%, e.g. 15% | Component of the nanoparticle |
| Factor VIIa inhibitors | 20-30%, e.g. 25% | Active ingredient (e.g., non-covalently encapsulated in or covalently linked to the L-poly-arginine nanoparticles) |
| Factor VIIa inhibitors-NO Donors | 20-100% | Active ingredient stand alone (100%) or encapsulated non-covalently or chemically conjugated covalently to the L-poly-arginine nanoparticles |
| Liposome | Outer shell (1-100 uM), average 10-20 uM | Encapsulate multiple nanoparticles formed by a-c |

The fatty acids that may be cross-linked with L-arginine may be unsaturated fatty acids such as:

Oleic acid: $CH_3(CH_2)_7CH=CH(CH_2)_7COOH$

Linoleic acid: $CH_3(CH_2)_4CH=CHCH_2CH=CH(CH_2)_7COOH$

α-Linoeic acid: $CH_3CH_2CH=CHCH_2CH=CHCH_2CH=CH(CH_2)_7COOH$

Docosahexaeonic acid: $CH_3CH_2CH=CHCH_2CH=CHCH_2CH=CHCH_2CH=CHCH_2CH=CH(CH_2)_2COOH$ The fatty acids that may be cross-linked with L-arginine may be saturated fatty acids such as the saturated fatty acids listed in Table 2 infra.

TABLE 2

Examples of Saturated Fatty Acids

| Common Name of Saturated Fatty Acids | Chemical Structure |
|---|---|
| Caprylic acid | $CH_3(CH_2)_6COOH$ |
| Capric acid | $CH_3(CH_2)_8COOH$ |
| Lauric acid | $CH_3(CH_2)_{10}COOH$ |
| Myristic acid | $CH_3(CH_2)_{12}COOH$ |
| Palmitic acid | $CH_3(CH_2)_{14}COOH$ |
| Stearic acid | $CH_3(CH_2)_{16}COOH$ |
| Arachidic acid | $CH_3(CH_2)_{18}COOH$ |
| Behenic acid | $CH_3(CH_2)_{20}COOH$ |
| Lignoceric acid | $CH_3(CH_2)_{22}COOH$ |
| Cerotic acid | $CH_3(CH_2)_{24}COOH$ |

The contents of the nanoparticles are confirmed using, for example, HPLC and LC/MS. The nanoparticle formulations may be sterilized using conventional means; e.g., filtration, gamma radiation.

In one embodiment, the present invention provides a method for treating pulmonary hypertension and pulmonary arterial hypertension. The method comprises administering an effective amount of a Factor VIIa inhibitors containing NO donor-nanoparticle formulation to a patient in need thereof, wherein the Factor VIIa inhibitors NO donor-nanoparticle comprises a biodegradable polymer.

In one embodiment, the invention provides a method for treating cardiac insufficiency; e.g., heart failure, angina, or acute myocardial infarction. The method comprises administering an effective amount of Factor VIIa inhibitors —NO donor nanoparticle formulation to a patient in need thereof, wherein the Factor VIIa inhibitors —NO donor nanoparticle comprises a biodegradable polymer.

In one example of the foregoing methods, the administered nanoparticle comprises Poly L-arginine nanoparticles encapsulating Factor VIIa inhibitors or Factor VIIa inhibitor-NO.

In an example, the Factor VIIa inhibitors or Factor VIIa inhibitors —NO donor nanoparticle administered comprises Poly L-arginine nanoparticles encapsulating Factor VIIa inhibitors or Factor VIIa inhibitors-NO donor with gluteraldehyde as a cross linker. Other cross-linkers may be used. In another example, the Factor VIIa inhibitors or Factor VIIa inhibitors-NO donor nanoparticle administered comprises Poly L-arginine-PLGA nanoparticles encapsulating Factor VIIa inhibitors. Such examples of Factor VIIa inhibitors or Factor VIIa inhibitors-NO donor nanoparticles may utilize a process that includes gelation/conjugation of preformed biodegradable polymers.

In an example, the Factor VIIa inhibitors or Factor VIIa inhibitors-NO donor nanoparticle administered includes Poly L-arginine-fatty acid conjugated nanoparticles immobilizing Factor VIIa inhibitors or Factor VIIa inhibitors-NO donor. Alternatively, the Factor VIIa inhibitors or Factor VIIa inhibitors-NO donor nanoparticles administered comprises Poly L-arginine nanoparticles immobilizing or covalently linking Factor VIIa inhibitors.

In an example, the factor VIIa inhibitor-nanoparticle formulation with poly L-arginine and its cross-linked moieties is encapsulated or conjugated to Poly L-arginine placed into liposomes and is administered by inhalation, oral, or injectable.

In one embodiment, administration is by a pump activated by a signal, which releases the nanoparticles into the bloodstream. In one embodiment the signal is generated when pulmonary arterial pressure rises above a given level; e.g., greater than 30, for example, greater than 40 mmHg, as measured by an electronic pressure transducer linked to a cannula in the pulmonary artery.

In one embodiment, the present invention employs a drug eluting stent, wherein the drug eluted comprises Factor VIIa inhibitors or Factor VIIa inhibitors—NO donor nanoparticles.

In one embodiment, the present invention employs inhalation delivery systems using liposome, which releases Factor VIIa inhibitors or Factor VIIa inhibitors—NO donor nanoparticles into the pulmonary tissues.

In one embodiment, the present invention employs oral delivery systems which release Factor VIIa inhibitors or Factor VIIa inhibitors—NO donor nanoparticles into the bloodstream, with site directed delivery to pulmonary tissues.

In one embodiment, the present invention employs injectable delivery systems which release Factor VIIa inhibitors or Factor VIIa inhibitors—NO donor nanoparticles into the bloodstream, with site directed delivery to pulmonary tissues.

The Factor VIIa inhibitors—NO donor and its nanoparticles of the present invention may be administered in conjunction with, or adjunctive to, the normal standard of care for pulmonary hypertension or cardiac insufficiency or other cardiovascular or neurological disorders, for example in conjunction with one or more of the followings:

(i) one or more drugs selected from the group consisting of endothelin receptor antagonists (e.g., bosentan, sitaxentan, ambrisentan), phosphodiesterase type 5 inhibitors (e.g., sildenafil, tadalafil), prostacyclin derivatives (e.g., epoprostenol, treprostenil, iloprost, beroprost), and/or soluble guanylate cyclase (sGC) activators (e.g., cinaciguat and riociguat);

(ii) diuretics (e.g., hydrochlorothiazide);

(iii) antiplatelets (e.g., aspirin);

(iv) calcium channel blockers (e.g., amlodipine)$_e$;

(v) beta-blockers (e.g. metoprolol);

(vi) ACE inhibitors (e.g. captopril, enalapril, lisinopril);

(vii) inhaled beta-agonists, corticosteroids, and/or anti-asthma drugs, (viii) angiotensin Receptor Blockers (e.g., Losartan).

Various methods of synthesizing Factor VIIa inhibitors or Factor VIIa inhibitors—NO donor nanoparticles are provided. For example, a single emulsion process may produce chitosan-PLGA nanoparticles encapsulating Factor VIIa inhibitors or Factor VIIa inhibitors—NO. In yet another example, a process involving gelation/con (Factor VIIa inhibitor IV in which the group $R_1$ can be located at one or more positions of positions 3, 4, and 5 as single, double, or triple substitutions).

For Factor VIIa inhibitors I, II, III, and IV, the group $R_1$ is either hydrogen (H) which is denoted as $R_{10}$ or any of the following NO donors:

$$O{=}N{-}S{-} \quad (R_{11})$$

$$-ONO_2 \quad (R_{12});$$

$$-CH_2ONO_2 \quad (R_{13});$$

$$-CH_2CH_2ONO_2 \quad (R_{14});$$

$$-C({=}NOH)(CH_2)_3ONO_2 \quad (R_{15});$$

$$-CH_2CH(ONH_2)CH_2ONO_2 \quad (R_{16});$$

$$(R_{17})$$

$$-\underset{H}{N}-\underset{|}{N}-N{=}O; \quad \text{with } O^-, M^+ \text{ on middle N}$$

$$(R_{18})$$

$$-HN-N^+\!\!\underset{N-O}{\overset{X^-}{\diagdown}}\!\!NH_2;$$

$$(R_{19})$$

[pyrrolidine N-diazeniumdiolate structure with methoxy group]

For Factor VIIa inhibitor II, the group $R_2$ is either hydrogen (H) (denoted as $R_{20}$) or any of the following NO donors:

$$O{=}N{-}S{-} \quad (R_{21});$$

$$-ONO_2 \quad (R_{22});$$

$$-CH_2ONO_2 \quad (R_{23});$$

$$-CH_2CH_2ONO_2 \quad (R_{24});$$

$$-C({=}NOH)(CH_2)_3ONO_2 \quad (R_{25});$$

$$-CH_2CH(ONH_2)CH_2ONO_2 \quad (R_{26});$$

$$(R_{27})$$

$$-\underset{H}{N}-\underset{|}{N}-N{=}O;$$

$$(R_{28})$$

$$-HN-N^+\!\!\underset{N-O}{\overset{X^-}{\diagdown}}\!\!NH_2;$$

-continued $$(R_{29})$$

[pyrrolidine N-diazeniumdiolate structure with methoxy group]

Any of the preceding Factor VIIa inhibitors I, II, III, and IV may be comprised by a nanoparticle of the present invention such that the nanoparticle comprises a poly L-arginine polymer and the Factor VIIa inhibitor (I, II, III, and/or IV) in the poly L-arginine polymer.

Any of the preceding Factor VIIa inhibitors I, II, III, and IV may be comprised by a chemical structure of the present invention such that the chemical structure comprises the Factor VIIa inhibitor (I, II, III, and/or IV) that includes at least one nitric oxide (NO) donor.

For the preceding Factor VIIa inhibitors I, II, III, and IV, the linkage of the NO donor to the poly L-arginine polymer is between the amino or carboxyl groups and the hydroxyl or other reactive group.

Figure 1A:
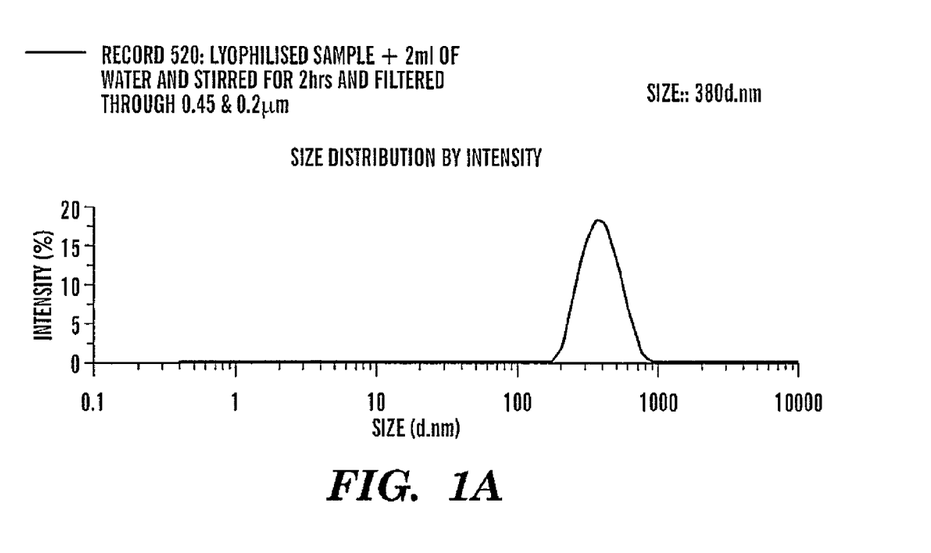
FIGS. 1A and 1B depict plots of the intensity of scattered nanoparticles versus (i) particle diameter size in nanometers (FIG. 1A) and (ii) Zeta potential due to surface charge (FIG. 1B), for Factor VIIa inhibitor (or Factor VIIa inhibitor—NO) encapsulated in polyarginine nanoparticles, in accordance with embodiments of the present invention.
Figure 1B:
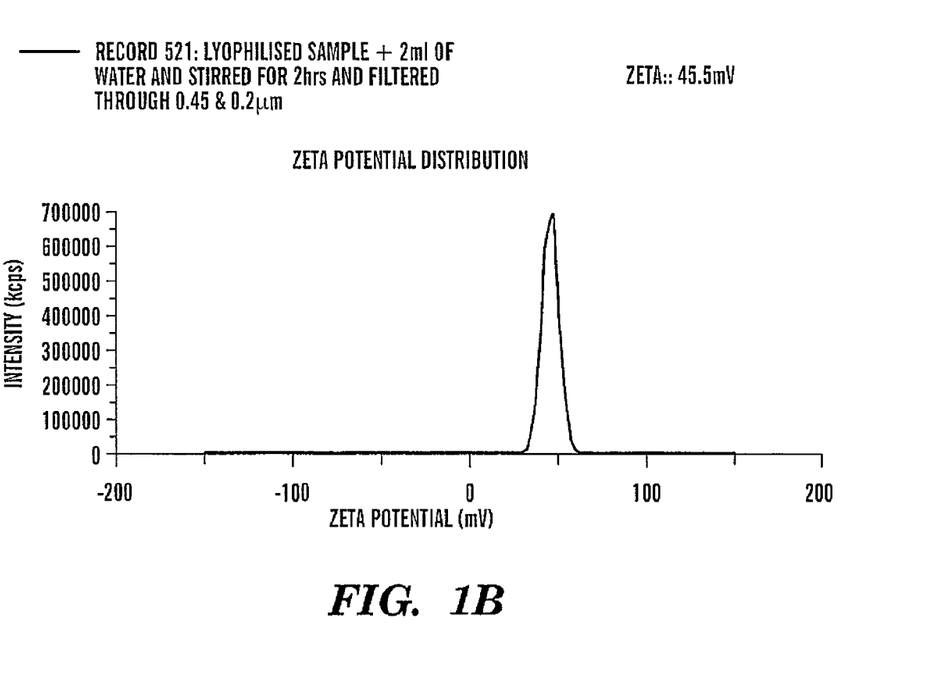

FIGS. 1A and 1B depict plots of the intensity of scattered nanoparticles versus (i) particle diameter size in nanometers (FIG. 1A) and (ii) Zeta potential due to surface charge (FIG. 1B), for Factor VIIa inhibitor (or Factor VIIa inhibitor—NO) encapsulated in polyarginine nanoparticles, in accordance with embodiments of the present invention. The plots of FIGS. 1A and 1B were derived from dynamic light scattering (DLS) measurements. The poly L-arginine nanoparticles encapsulating either Factor VIIa inhibitors or Factor VIIa inhibitors—NO donor may be optimized as to size and entrapment efficiency to get an optimum formulation with maximum loading based on the Factor VIIa inhibitor, Factor VIIa inhibitors—NO donor, or other active compounds to be utilized. The measured average diameter size is 380 nanometers and the average measured Zeta potential is 45.5 millivolts.

Figure 2A:
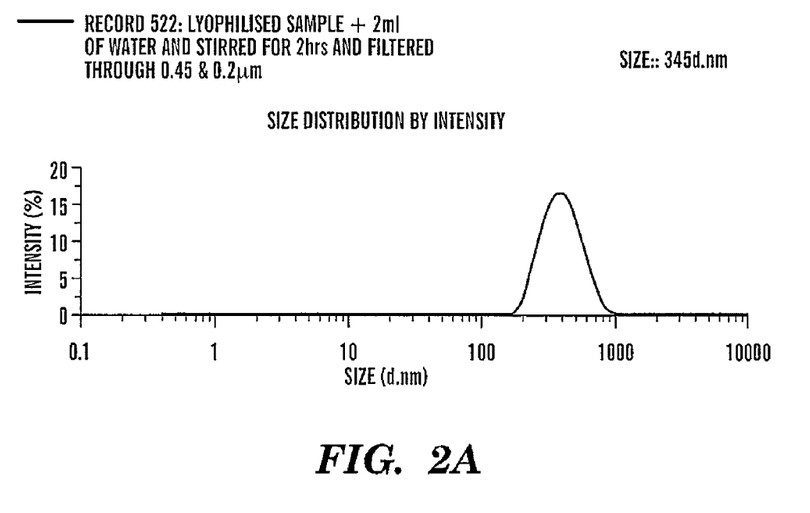
FIGS. 2A and 2B depict the intensity of scattered nanoparticles versus (i) particle diameter size in nanometers (FIG. 2A) and Zeta potential due to surface charge (FIG. 2B, for Factor VIIa inhibitor (or Factor VIIa inhibitor—NO) encapsulated in poly L-arginine (PLA)—fatty acid (lauric acid) nanoparticles, in accordance with embodiments of the present invention.
Figure 2B:
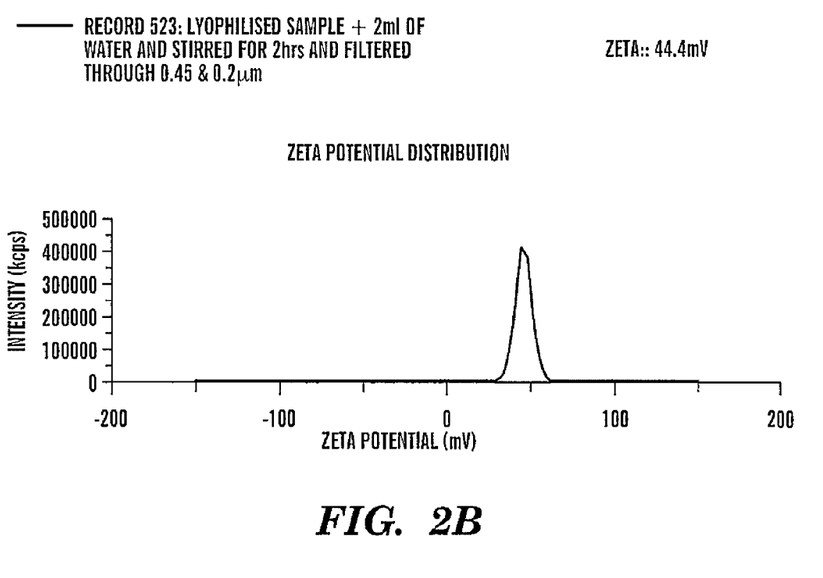

FIGS. 2A and 2B depict the intensity of scattered nanoparticles versus (i) particle diameter size in nanometers (FIG. 2A) and Zeta potential due to surface charge (FIG. 2B, for Factor VIIa inhibitor (or Factor VIIa inhibitor—NO) encapsulated in poly L-arginine—fatty acid (lauric acid) nanoparticles, in accordance with embodiments of the present invention. The plots of FIGS. 2A and 2B were derived from dynamic light scattering (DLS) measurements. The measured average diameter size is 345 nanometers and the average measured Zeta potential is 44.4 millivolts.

Figure 3A:
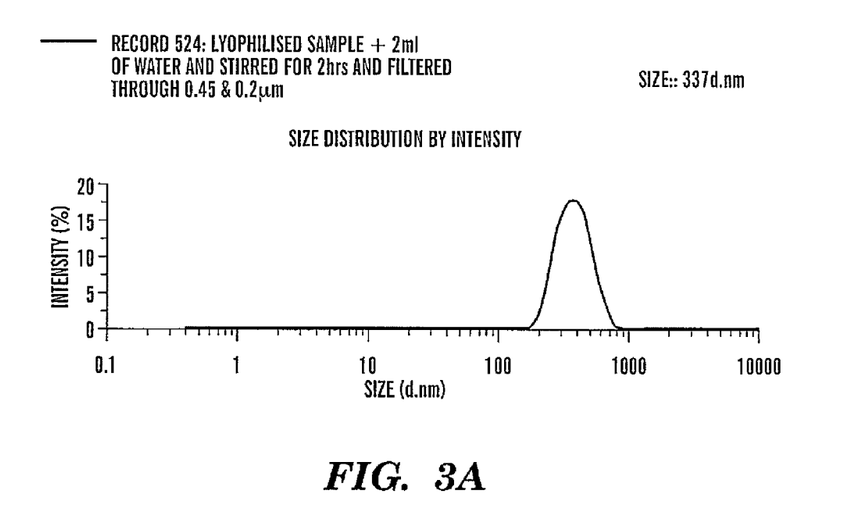
FIGS. 3A and 3B depict the intensity of scattered nanoparticles versus (i) particle diameter size in nanometers (FIG. 3A) and (ii) Zeta potential due to surface charge (FIG. 3B), for Factor VIIa inhibitor (or Factor VIIa inhibitor—NO) encapsulated in gluteraldehyde crosslink poly L-arginine nanoparticles, in accordance with embodiments of the present invention.
Figure 3B:
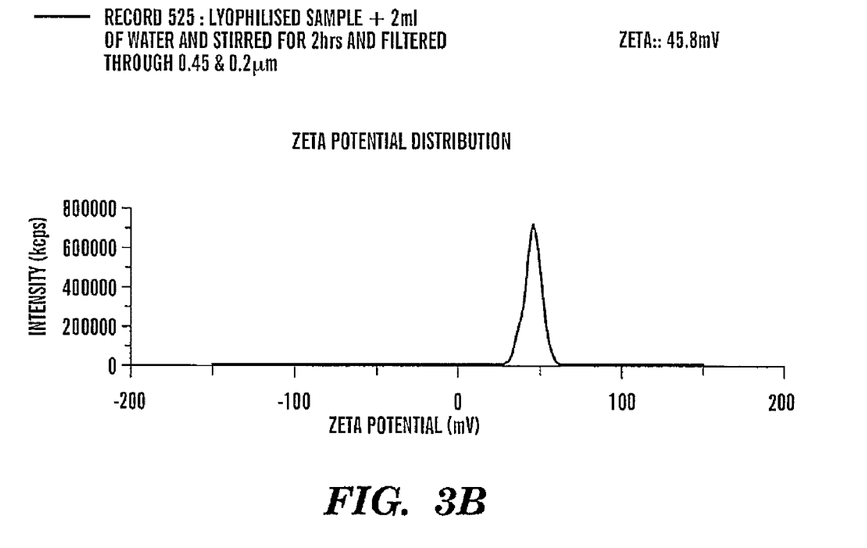

FIGS. 3A and 3B depict the intensity of scattered nanoparticles versus (i) particle diameter size in nanometers (FIG. 3A) and (ii) Zeta potential due to surface charge (FIG. 3B); for Factor VIIa inhibitor (or Factor VIIa inhibitor—NO) encapsulated in gluteraldehyde crosslink poly L-arginine nanoparticles, in accordance with embodiments of the present invention. The plots of FIGS. 3A and 3B were derived from dynamic light scattering (DLS) measurements. The measured average diameter size is 337 nanometers and the average measured Zeta potential is 45.8 millivolts.

Figure 4:
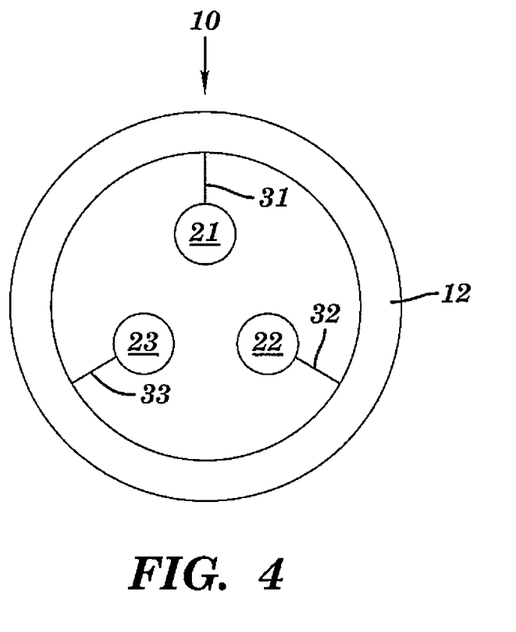
FIG. 4 depicts a nanoparticle, comprising a poly L-arginine polymer and Factor VIIa inhibitors conjugated to the poly L-arginine polymer and covalently bonded to the poly L-arginine polymer via covalent bonds, in accordance with embodiments of the present invention.

FIG. 4 depicts a nanoparticle 10, comprising a poly L-arginine polymer 12 and Factor VIIa inhibitors 21, 22, and 23 conjugated to the poly L-arginine polymer 12 and covalently bonded to the poly L-arginine polymer 12 via covalent bonds 31, 32, and 33, respectively, in accordance with embodiments of the present invention. The Factor VIIa inhibitors 21, 22, and 23 may be any of the Factor VIIa inhibitors identified supra, which includes Factor VIIa inhibitors with or without at least one NO donor. Although three Factor VIIa inhibitors (21, 22, 23) are depicted in FIG. 4, the nanoparticle 10 may generally comprise N1 Factor VIIa inhibitors such that N1 is a positive integer of at least 1.

Figure 5:
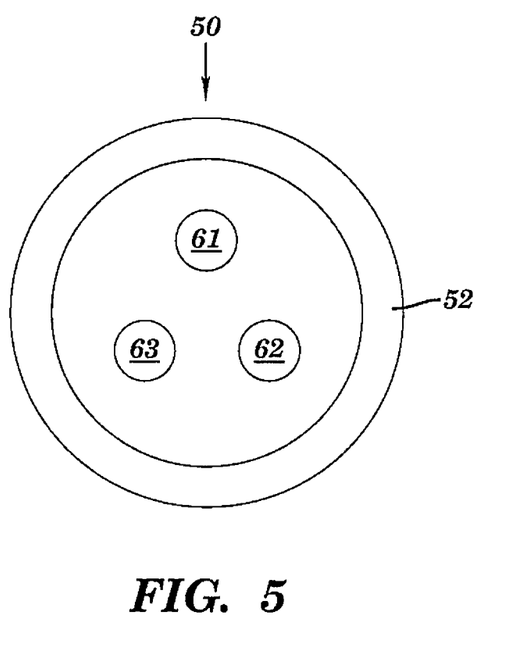
FIG. 5 depicts a nanoparticle, comprising a poly L-arginine polymer and Factor VIIa inhibitors encapsulated in the poly L-arginine polymer and not covalently bonded to the poly L-arginine polymer, in accordance with embodiments of the present invention.
Figure 6:
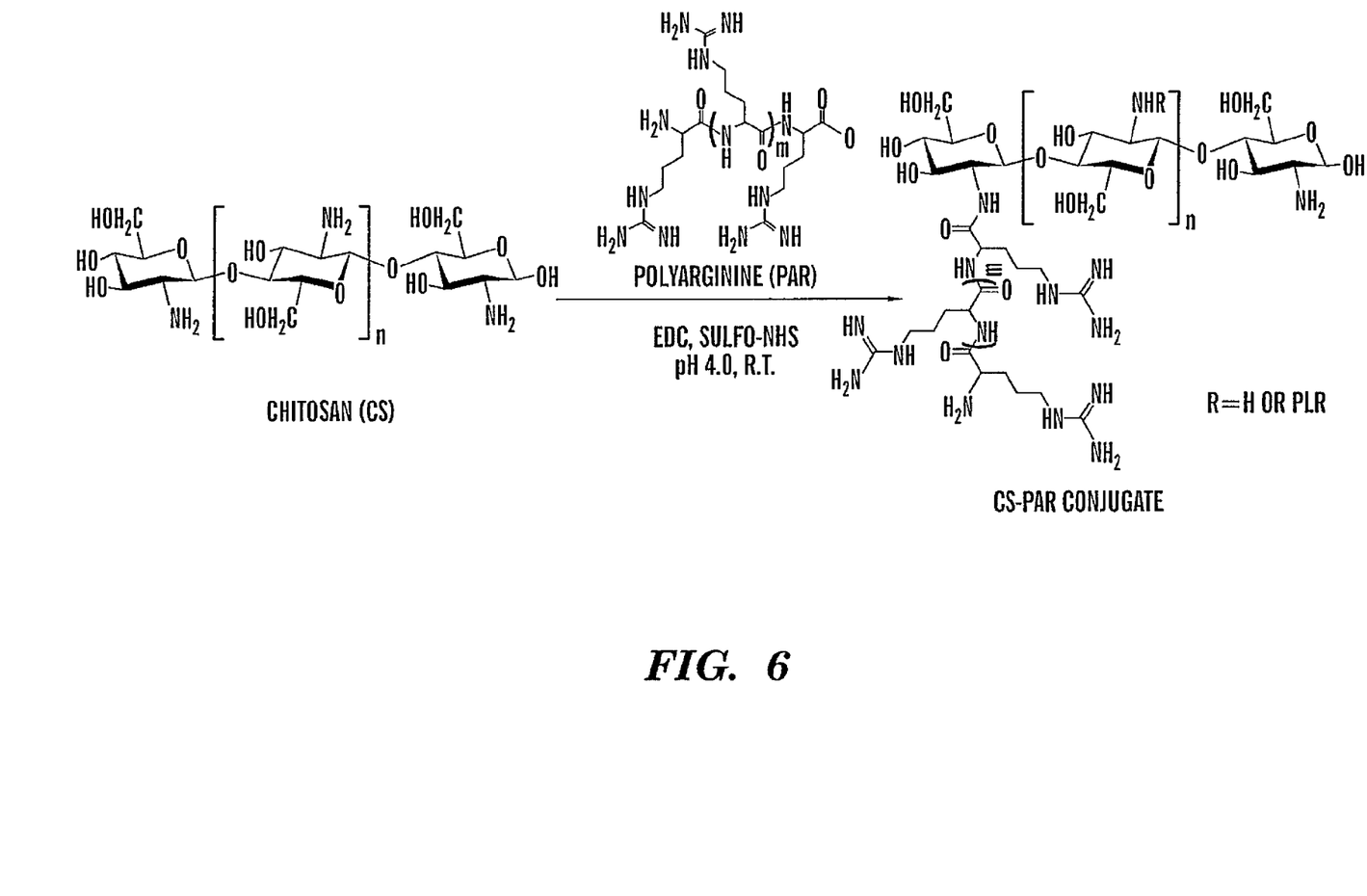
FIG. 6 depicts synthesis of chitosan-polyarginine conjugate, in accordance with embodiments of the present invention.

FIG. 5 depicts a nanoparticle 50, comprising a poly L-arginine polymer 52 and Factor VIIa inhibitors 61, 62, and 63 encapsulated in the poly L-arginine polymer 52 and not covalently bonded to the poly L-arginine polymer 52, in accordance with embodiments of the present invention. The Factor VIIa inhibitors 61, 62, and 63 may be any of the Factor VIIa inhibitors identified supra, which includes Factor VIIa inhibitors with or without at least one NO donor. Although three Factor VIIa inhibitors (61, 62, 63) are depicted in FIG. 5, the nanoparticle 50 may generally comprise N2 Factor VIIa inhibitors such that N2 is a positive integer of at least 1.

Factor VIIa inhibitors or Factor VIIa inhibitors—NO donor encapsulated in nanoparticles with different degree of cross linking are tested for optimal pharmacokinetics. The formulation is optimized for loading efficiency. The ratios of different constituents are manipulated for optimum delayed release. To achieve that goal, the following parameters are evaluated: (i) particle size analysis by DLS spectroscopy; (ii) zeta potential measurement; (iii) in vitro release kinetics; (iv) Transmission Electron Microscopy for size confirmation, measurement of Factor VIIa inhibitors or Factor VIIa inhibitors—NO donor inside the nanoparticles (by HPLC or LC/MS).

Releasing NO from Polyarginine nanoparticles and its cross-linked materials having factor VIIa inhibitor encapsulated or Factor VIIa inhibitors conjugated with NO donors may be used for treating vascular disorders including pulmonary hypertension, pulmonary arterial hypertension, sickle cell disorders and other vascular disorders. Such nanoparticles provide improved delivery of Factor VITA inhibitor-NO donor and allow for acute treatment and optionally for sustained release of Factor VIIA inhibitor-NO donor in a patient.

The long acting effective Factor VIIa inhibitors in nanoformulations that generate NO or Factor VIIa conjugated to NO donors, as provided in the present invention, expands the scope of aerosol (inhalation), oral and injectable therapies for treatment of pulmonary and other systemic vascular diseases such as sickle cell, peripheral artery diseases, critical limb ischemia, acute coronary syndrome, stroke, ischemia, and other vascular disorders.

SYNTHESIS EXAMPLES

Example 1

Synthesis of Factor VIIa Inhibitors or Factor VIIa Inhibitors-NO Donor Encapsulated Nanoparticles Nanoparticles encapsulating Factor VIIa inhibitors of the present invention are produced using a reverse micelle method where chitosan polymer and Factor VIIa inhibitors or Factor VIIa inhibitors. NO donors are added to Dimethysulfoxide (DMSO) and surfactant solution to form reverse micelles. Bifunctional reagent gluteraldehyde is added to this reverse micelles system as a cross-linking agent. The chemical cross-linking of poly L-arginine polymers with gluteraldehyde occurs by Schiff's reaction of aldehyde group on gluteraldehyde and amino group on the chitosan chain. Finally nanoparticles are separated out by high speed centrifugation.

Example 2

Synthesis of Poly L-Arginine—PLGA Nanoparticles

Factor VIIa inhibitors or Factor VIIa inhibitors—NO donor PLA-PLGA hybrid nanoparticles are prepared according to the same scheme shown in Example 1.

Example 3

Synthesis of Hydrophobic Poly L-Arginine with Site Directed Delivery to Pulmonary Tissues Conjugation of ligand to the integrin αvβ3 such as cyclic N-Methyl-Arginine-Glycine-Aspartic acid (N-ME-Arg-Gly-Asp), and other known high affinity ligands to αv integrin.

Example 4

Synthesis of Hydrophobic Chitosan Polymer

Hydrophobic chitosan polymer is synthesized by cross-linking to fatty acids, amino acid, bile acid, poly glycol lactic acid, and other acids.

Example 5

Synthesis of Polyarginine Cross Linked Nanoparticles

Nanoparticle formulations of Polyarginine with fatty acid, bile acid, bile salt, chitosan, PLGA or other amino acids were stirred, centrifuged, dialyzed, and Lyophilized. The lyophilized nanoformulations were measured for size and zeta potential by dispersing it in double distilled water or phosphate buffered saline. Nanoformulations were sonicated and stirred, checked repeatedly over time for size and Zeta potential.

Example 6

Synthesis of Chitosan (CS) Polyarginine (PAR) Conjugate (CS-PAR)

The Chitosan polyarginine (CS-PAR) conjugates are synthesized where the conjugation is achieved by amide bond linkage between the amine group (—$NH_2$) of CS and the carboxyl group (—COOH) of PAR. Briefly, for conjugation of CS and PAR, 5 ml of CS solution (1 mg/ml) is mixed with 5 ml of PLR (1 mg/ml) and then added to 800 mg of 1-ethyl-3-(3-dimethylaminopropyl) carbodiimide hydrochloride (EDC) and 1 gram of N-hydroxysulfosuccinimide (Sulfo-NHS). After 24 hours, the resulting CS-PLR conjugates are separated by membrane-filter. Further dialysis will be performed for purification. The final solution is lyophilized for further studies.

FIG. 6 depicts synthesis of chitosan-polyarginine conjugate, in accordance with embodiments of the present invention. The number of repeating unit (n) is in a range of 20-1000. The number of repeating units (m) is in a range of 10-500.

The same protocol is used for the conjugation of Polyarginine with PLGA (having $NH_2$ functional groups) via the COOH of the polyarginine. Additionally, conjugation of polyarginine with fatty acids or bile acids is through the $NH_2$ of the polyarginine.

Example 7

Synthesis of Chitosan-Polyarginine Nanoparticles (CS-PAR-NPs)

A Chitosan-Polyarginine nanoparticle (CS-PAR-NPs) is synthesized in mild acidic conditions by promoting the interaction of the $NH_3$ group present in chitosan with the phosphate group present in tripolyphosphate (TPP). Briefly, to 10 ml of a solution 1% CS-PAR conjugate, 1 ml of a triphosphate disodium salt (1 mg/ml in DI water) is added drop by drop, with constant stirring. The entire solution is then sonicated for about 30 seconds using a probe sonicator, and allowed to stir for another 4 hours (approx). This solution is lyophilized to get the nanoformulation in powdered form. The lyophilized powder will be re-dispersed in phosphate buffered for further use.

Example 8

Synthesis of Factor VIIa Inhibitors with Poly-L-arginine

Poly L-arginine (PAR) and Factor VIIa inhibitors are immersed in a 1% solution including (fatty acid, bile acid, amino acid, PLGA or chitosan), followed by stirring and sonicating; and performing a dialysis step, to yield the Factor VIIa inhibitors. The formed PAR layer formed in the Factor VIIa inhibitor may be cross linked with a cross linker (e.g., gluteraldehyde).

While particular embodiments of the present invention have been described herein for purposes of illustration, many modifications and changes will become apparent to those skilled in the art. Accordingly, the appended claims are intended to encompass all such modifications and changes as fall within the true spirit and scope of this invention.

What is claimed:

1. A nanoparticle, comprising a poly L-arginine polymer and a Factor VIIa inhibitor conjugated to or encapsulated in the poly L-arginine polymer, wherein the Factor VIIa inhibitor is

which is Factor VIIa inhibitor I in which $R_1$ is independently selected from the group consisting of hydrogen and a NO donor at positions 3, 4, 5, and 6,

which is Factor VIIa inhibitor II in which $R_1$ is independently selected from the group consisting of hydrogen and a NO donor at positions 3, 4, and 6 and in which $R_2$ is independently selected from the group consisting of hydrogen and a NO donor at positions 2, 4, 5, and 6,

which is Factor VIIa inhibitor III in which $R_1$ is independently selected from the group consisting of hydrogen and a NO donor at positions 3, 4, 5, and 6, or

which is Factor VIIa inhibitor IV in which $R_1$ is independently selected from the group consisting of hydrogen and a NO donor at positions 3, 4, and 5, wherein for each position in each Factor VIIa inhibitor of Factor VIIa inhibitors I, II, III, and IV, at which $R_1$ is independently selected as the NO donor, the NO donor is selected independently from the group consisting of $O{=}N{-}S{-}$ ($R_{11}$)

$-ONO_2$ ($R_{12}$);

$-CH_2ONO_2$ ($R_{13}$);

$-CH_2CH_2ONO_2$ ($R_{14}$);

$-C({=}NOH)(CH_2)_3ONO_2$ ($R_{15}$);

$-CH_2CH(ONH_2)CH_2ONO_2$ ($R_{16}$);

(R$_{17}$)

(R$_{18}$)

(R$_{19}$)

and wherein for each position in Factor VIIa inhibitors II at which R$_2$ is independently selected as the NO donor, the NO donor is selected independently from the group consisting of R$_{11}$, R$_{12}$, R$_{13}$, R$_{14}$, R$_{15}$, R$_{16}$, R$_{17}$, R$_{18}$, and R$_{19}$.

2. The nanoparticle of claim 1, wherein the Factor VIIa inhibitor does not include any nitric oxide (NO) donor.

3. The nanoparticle of claim 1, wherein the Factor VIIa inhibitor includes at least one nitric oxide (NO) donor.

4. The nanoparticle of claim 1, wherein the Factor VIIa inhibitor is conjugated to the poly L-arginine polymer by being covalently bonded to the poly L-arginine polymer.

5. The nanoparticle of claim 1, wherein the Factor VIIa inhibitor is encapsulated in the poly L-arginine polymer (R17)

(R18)

(R19)

and wherein for each position in Factor VIIa inhibitors II at which $R_2$ is independently selected as the NO donor, the NO donor is selected independently from the group consisting of $R_{11}$, $R_{12}$, $R_{13}$, $R_{14}$, $R_{15}$, $R_{16}$, $R_{17}$, $R_{18}$, and $R_{19}$.

* * * * *